United States Patent
Kishore Prasad et al.

(10) Patent No.: US 9,656,927 B2
(45) Date of Patent: May 23, 2017

(54) PROCESS FOR THE SYNTHESIS OF CARBOXYLIC ACID DERIVATIVES

(71) Applicant: COUNCIL OF SCIENTIFIC & INDUSTRIAL RESEARCH, New Delhi (IN)

(72) Inventors: Pragati Kishore Prasad, Maharashtra (IN); Arumugam Sudalai, Maharashtra (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/033,323

(22) PCT Filed: Nov. 3, 2014

(86) PCT No.: PCT/IN2014/000703
§ 371 (c)(1),
(2) Date: Apr. 29, 2016

(87) PCT Pub. No.: WO2015/063798
PCT Pub. Date: May 7, 2015

(65) Prior Publication Data
US 2016/0272554 A1    Sep. 22, 2016

(30) Foreign Application Priority Data
Nov. 1, 2013  (IN) .......................... 3239/DEL/2013

(51) Int. Cl.
| | | |
|---|---|---|
| C07B 41/12 | (2006.01) |
| C07C 67/00 | (2006.01) |
| C07D 311/76 | (2006.01) |
| C07D 491/052 | (2006.01) |
| C07D 209/46 | (2006.01) |
| C07C 51/00 | (2006.01) |
| C07D 307/88 | (2006.01) |
| C07D 307/89 | (2006.01) |
| C07C 201/12 | (2006.01) |
| C07C 231/12 | (2006.01) |
| C07D 311/10 | (2006.01) |
| C07C 231/10 | (2006.01) |
| C07D 209/48 | (2006.01) |
| C07B 43/06 | (2006.01) |

(52) U.S. Cl.
CPC .............. *C07B 41/12* (2013.01); *C07B 43/06* (2013.01); *C07C 51/00* (2013.01); *C07C 67/00* (2013.01); *C07C 201/12* (2013.01); *C07C 231/10* (2013.01); *C07C 231/12* (2013.01); *C07D 209/46* (2013.01); *C07D 209/48* (2013.01); *C07D 307/88* (2013.01); *C07D 307/89* (2013.01); *C07D 311/10* (2013.01); *C07D 311/76* (2013.01); *C07D 491/052* (2013.01)

(58) Field of Classification Search
CPC ......... C07B 41/12; C07B 43/06; C07C 51/00; C07C 67/00; C07C 201/12; C07C 231/10; C07C 231/12; C07D 209/46; C07D 209/48; C07D 311/10; C07D 311/76; C07D 307/88; C07D 307/89; C07D 491/052

See application file for complete search history.

(56) References Cited

PUBLICATIONS

T.P. Yoon et al., "Product Subclass 10: Arenecarboxylic Acids", Science of Synthesis, Jan. 1, 2006, pp. 533-549.
H. Cristau et al., "Mild and Efficient Copper-Catalyzed Cayanation of Aryl Iodides and Bromides", Chemistry—A European Journal, Apr. 8, 2005, vol. 11, No. 8, pp. 2483-2492.
J. Zanon et al., "Cooper-Catalyzed Domino Halide Exchange-Cyanation of Aryl Bromides", Journal of the American chemical Society, Mar. 1, 2003, vol. 125, No. 10, pp. 2890-2891.
M. F. Semmelhack, et al., "Intramolecular Carbonylation of Vinyl Halides to Form Methylene Lactones", J. Org. Chem., 1981, pp. 1723-1726, vol. 46, No. 8.
Yewen Fang, et al., "Preference of 4-exo Ring Closure in Cooper-Catalyzed Intramolecular Coupling of Vinyl Bromides with Alcohols", J. Am. Chem. Soc., 2007, pp. 8092-8093, vol. 129.
Anne Brennführer, et al., "Palladium-Catalyzed Carbonylation Reactions of Aryl Halides and Related Compounds", Angew. Chem. Int. Ed., 2009, pp. 4114-4133, vol. 48, Wiley-VCH Verlag GmbH & Co KGaA, Weinheim, DE.

Primary Examiner — D M Seaman
(74) Attorney, Agent, or Firm — Baker and Hostetler LLP

(57) ABSTRACT

The present invention discloses one-pot synthesis of various carboxylic acid derivatives using copper catalyst and sodium cyanide as the cyanide source for bringing in carbonylative coupling in a single step.

7 Claims, No Drawings

PROCESS FOR THE SYNTHESIS OF CARBOXYLIC ACID DERIVATIVES

CROSS REFERENCE TO RELATED APPLICATIONS

This application is a National Stage of International Application No. PCT/IN2014/000703, filed on Nov. 3, 2014, which claims priority to Indian patent application no. 3239/DEL/2013, filed on Nov. 1, 2013, the disclosures of which are incorporated by reference in their entirety.

FIELD OF THE INVENTION

The present invention relates to copper catalyzed preparation of various carboxylic acid derivatives using sodium cyanide as the cyanide source for bringing in carbonylative coupling in a single step.

BACKGROUND AND PRIOR ART OF THE INVENTION

Aromatic esters are important building blocks for various pharmaceuticals and agrochemicals, whereas phenyl esters are widely used in liquid crystals, photosensitizers and biologically active compounds. Aromatic amides are an important functional group of various natural products and designed pharmaceutical molecules. Some heterocyclic amides are potential CNS (central nervous system)-active compounds.

Traditionally, these esters were synthesized via reaction of the carboxylic acid with alcohols or phenols. Carbonylation of the aryl halides in the presence of an alcohol/phenol is an attractive alternative method that tolerates a wide range of substrates, thus demonstrating a great advantage for the synthesis of substituted aromatic esters and its derivatives. In this regard, various palladium-based catalytic systems, such as $Pd(OAc)_2$, 10 $PdCl_2(PhCN)_2$ with ferrocenyl phosphine ligand, and $Pd(OAc)_2/PPh_3$ in the presence of an ionic liquid, have been explored for alkoxycarbonylation and phenoxycarbonylation reactions. A variety of palladium-based homogeneous catalytic systems, such as $PdBr_2(PPh_3)_2/PdCl_2(PPh_3)_2$, $Pd(dppp)Cl_2$, palladium-1,3-bis(dicyclohexyl-phosphino)propane-$H_2BF_4$, 16 and $Pd(OAc)_2$/xantphos catalytic system, were used for this reaction. Amino carbonylation using an ionic liquid and Pd $(OAc)_2/PPh_3$ was explored by kollar and co-workers. However, these methods are plagued with: (i) Less functional group tolerance due to acidic and basic reaction conditions (ii) use or liberation of inflammable, toxic and explosive CO gas (iii) Use of expensive phosphine ligands or NHC catalysts and (iv) Need of heavy transition metal like Pd. Therefore, the industrial applicability of these processes is limited by the inherent problem of catalyst separation from the product as the palladium residues in the product stream could be a serious issue in the pharmaceutical industry.

Article titled "Intramolecular carbonylation of vinyl halides to form methylene lactones" by M. F. Semmelhack et al. *J. Org. Chem.*, 1981, 46 (8), pp 1723-1726 reports intramolecular carbonylation of vinyl halides to obtain methylene lactones with convenient nickel reagent and preliminary applications in a two-step cyclization-carbonylation procedure.

Article titled "Preference of 4-exo ring closure in copper-catalyzed intramolecular coupling of vinyl bromides with alcohols" by Y Fang et al. published in *J. Am. Chem. Soc.*, 2007, 129, 8092-8093 reports intramolecular O-vinylation of γ-bromohomoallylic alcohols with 10 mol % of CuI as the catalyst and 20 mol % of 1,10-phenanthroline as the ligand in refluxing MeCN led to the convenient formation of the corresponding 2-methyleneoxetanes in good to excellent yields via a 4-exo ring closure. 4-exo cyclization is preferred over other modes of cyclization. The products 2-methyleneoxetanes are obtained by coupling reaction.

Article titled "Palladium-catalyzed carbonylation reactions of aryl halides and related compounds" by A Brennführer et al. published in *Angew Chem Int Ed Engl.*, 2009; 48(23), 4114-33 reports the review summarizes recent work in the area of palladium-catalyzed carbonylation reactions of aryl halides and related compounds. Palladium-catalyzed carbonylation reactions of aromatic halides in the presence of various nucleophiles have undergone rapid development such that nowadays a plethora of palladium catalysts are available for different carbonylative transformations. The carboxylic acid derivatives, aldehydes, and ketones prepared in this way are important intermediates in the manufacture of dyes, pharmaceuticals, agrochemicals, and other industrial products.

Article titled "Mild and efficient copper-catalyzed cyanation of aryl iodides and bromides' by H J Cristau et al. published in *Chemistry*, 2005 Apr. 8; 11(8): 2483-92 reports an efficient copper-catalyzed cyanation of aryl iodides and bromides. The system combines catalytic amounts of both copper salts and chelating ligands. The latter, which have potential nitrogen- and/or oxygen-binding sites, have never previously been used in this type of reaction. A protocol has been developed that enables the cyanation of aryl bromides through the copper-catalyzed in situ production of the corresponding aryl iodides using catalytic amounts of potassium iodide. Aryl nitriles are obtained in good yields and excellent selectivities in relatively mild conditions (110° C.) compared with the Rosenmund-von Braun cyanation reaction. Furthermore, the reaction is compatible with a wide range of functional groups including nitro and amino substituents.

Article titled "Copper-catalyzed domino halide exchange-cyanation of aryl bromides" by J Zanon et al. published in *J. Am. Chem. Soc.*, 2003, 125, 2890-2891 reports an efficient, mild, and inexpensive copper-catalyzed domino halogen exchange-cyanation procedure for aryl bromides. The new method represents a significant improvement over the traditional Rosenmund-von Braun reaction: the use of catalytic amounts of copper and a polar solvent greatly simplifies the isolation and purification. In addition, the new method exhibits excellent functional group compatibility.

In the light of above, there is a need in the art to provide a simple, effective and unified process for production of carboxylic acid derivatives. Accordingly, the inventors have developed a high yielding and operationally simple carbonylation process for the synthesis of acid derivatives starting from aryl/vinyl/alkyl halides in a single step under neutral reaction conditions without the use of hazardous carbon monoxide. Considering cyanide to be isoelectronic with CO, the present inventors have preferred to choose NaCN as it is a cheap, robust, water soluble, easy to handle and does not produce any undesirable waste (unlike stoichiometric use of CuCN).

OBJECTIVE OF INVENTION

The main objective of the present invention is to provide a one-step, one-pot process for the synthesis of carboxylic acid derivative by carbonylative coupling in presence of copper bromide, sodium cyanide and 1,10-phenanthroline.

SUMMARY OF THE INVENTION

Accordingly, present invention provides a one-step, one-pot process for the synthesis of carboxylic acid derivatives comprising the steps of:
  a. stirring the solution of 0.9-1.1 equiv substituted halides in polar solvent optionally in presence of 0.9-1.3 equiv nucleophile followed by addition of 1.0-1.2 equiv sodium cyanide and 10-20 mol % of 1,10-phenanthroline and 5-25 mol % of copper bromide;
  b. quenching the reaction mixture of step (a) to obtain carboxylic acid derivatives.

In an embodiment of the present invention, substituted halides are selected from the group consisting of bromobenzene, 3-bromo-toluene, 4-methoxy-bromobenzene, 4-nitro-iodobenzene, 1-(2-bromophenyl)pent-4-en-2-ol, 1-(2-bromo-5-methylphenyl)pent-4-en-2-ol, 1-(2-bromo-5-methoxyphenyl)pent-4-en-2-ol, 1-(2-bromo-5-fluorophenyl)pent-4-en-2-ol, 1-(2,6-dibromo-3,4,5-trimethoxyphenyl)pent-4-en-2-ol, 1-(2-bromopyridin-3-yl)pent-4-en-2-ol, 2-(2,2-dibromovinyl)phenol, 1-(2-bromo-5-fluorophenyl)but-3-en-1-ol, 1-(2-bromo-5-methoxyphenyl)but-3-en-1-ol, 1-(2,5-dibromophenyl)but-3-en-1-ol, 1-(2-bromophenyl)octan-1-ol, 1-(2-bromophenyl)pentan-1-ol, 2-iodobenzoic acid, 1,2-dibromobenzene, (2-bromophenyl)methanamine.

In another embodiment of the present invention, nucleophile is selected from the group consisting of water, phenol, 4-nitro-phenol, 4-methoxybenzyl alcohol, aniline, 2-chloro-aniline, 4-methoxy-aniline, 2-chloro-benzylamine.

In yet another embodiment of the present invention, carboxylic acid derivatives are selected from the group consisting of phenyl benzoate, 4-nitrophenyl benzoate, 4-methoxybenzyl benzoate, N-phenylbenzamide, N-(2-chlorophenyl)benzamide, N-(2-chlorobenzyl)benzamide, benzoic acid, phenyl 3-methylbenzoate, phenyl 4-methoxybenzoate, phenyl 4-nitrobenzoate, 3-allylisochroman-1-one, 3-allyl-7-methylisochroman-1-one, 3-allyl-6-methoxyisochroman-1-one, 3-allyl-6-fluoroisochroman-1-one, 6,7,8-trimethoxy-1-oxoisochromane-5-carbonitrile, 6-allyl-5,6-dihydro-8H-pyrano[3,4-b]pyridin-8-one, 2H-chromen-2-one, 3-allyl-5-fluoroisobenzofuran-1(3H)-one, 3-allyl-5-methoxyisobenzofuran-1(3H)-one, 5-bromoisobenzofuran-1(3H)-one, 3-heptylisobenzofuran-1(3H)-one, 3-butylisobenzofuran-1(3H)-one, isobenzofuran-1,3-dione, 2-benzylisoindoline-1,3-dione.

In yet another embodiment of the present invention, the stirring is carried out at temperature ranges from 100° C. to 120° C.

In yet another embodiment of the present invention, stirring in step (a) is carried out for the period ranges from 10-12 hrs.

In yet another embodiment of the present invention, the polar solvent used is dimethylformamide (DMF).

In yet another embodiment of the present invention, quenching in step (b) is carried out using water.

In yet another embodiment of the present invention, yield is in the range of 63 to 96%.

DETAILED DESCRIPTION OF THE INVENTION

Present invention provides a high yielding and operationally simple method of preparation of acid derivatives starting from substituted halide in a single step under neutral reaction conditions.

Present invention provides a one-step, one-pot process for the synthesis of carboxylic acid derivatives comprising the steps of:
  a) Stirring the solution of substituted halides in polar solvent optionally in presence of phenols or alcohols or amines or water as nucleophile followed by addition of sodium cyanide, 1,10-phenanthroline and copper bromide;
  b) Quenching the reaction mixture of step (a) to obtain carboxylic acid derivatives.

The intermolecular O, N substituted nucleophiles are selected from benzyl amine, p-hydroxy benzaldehyde, substituted or unsubstituted phenols such as phenol, chlorophenol and the like.

Substituted halides are selected from bromobenzene, 3-bromo-toluene, 4-methoxy-bromobenzene, 4-nitro-iodobenzene, 1-(2-bromophenyl)pent-4-en-2-ol (2l), 1-(2-bromo-5-methylphenyl)pent-4-en-2-ol (2m), 1-(2-bromo-5-methoxyphenyl)pent-4-en-2-ol (2n), 1-(2-bromo-5-fluorophenyl)pent-4-en-2-ol (2o), 1-(2,6-dibromo-3,4,5-trimethoxyphenyl)pent-4-en-2-ol (2p), 1-(2-bromopyridin-3-yl)pent-4-en-2-ol (2q), 2-(2,2-dibromovinyl)phenol (2r), 1-(2-bromo-5-fluorophenyl)but-3-en-1-ol (2s), 1-(2-bromo-5-methoxyphenyl)but-3-en-1-ol (2t), 1-(2,5-dibromophenyl)but-3-en-1-ol (2u), 1-(2-bromophenyl)octan-1-ol (2v), 1-(2-bromophenyl)pentan-1-ol (2w), 2-iodobenzoic acid (2x), 1,2-dibromobenzene (2y), (2-bromophenyl)methanamine (2z) and the nucleophile is selected from phenol, 4-nitro-phenol, 4-methoxy benzyl alcohol, aniline, 2-chloro-aniline, 4-methoxy-aniline, 2-chloro-benzylamine.

The carboxylic acid derivatives that can be prepared using the process of the invention may be selected from esters, amides, chroman-1-one, isochroman-1-one, benzofuran-2(3H)-one, isobenzofuran-1,3-dione, isoindoline-1,3-dione, isoindoline 1-one compounds etc.

The carboxylic acid derivatives are selected from phenyl benzoate, 4-nitrophenyl benzoate, 4-methoxybenzyl benzoate, N-phenylbenzamide, N-(2-chlorophenyl)benzamide, N-(2-chlorobenzyl)benzamide, benzoic acid, phenyl 3-methylbenzoate, phenyl 4-methoxybenzoate, phenyl 4-nitrobenzoate, 3-allylisochroman-1-one, 3-allyl-7-methylisochroman-1-one, 3-allyl-6-methoxyisochroman-1-one, 3-ally-6-fluoro isochroman-1-one, 6,7,8-trimethoxy-1-oxoisochromane-5-carbonitrile, 6-allyl-5,6-dihydro-8H-pyrano[3,4-b]pyridin-8-one, 2H-chromen-2-one, 3-ally-5-fluoroisobenzofuran-1(3H)-one, 3-allyl-5-methoxyisobenzofuran-1(3H)-one, 5-bromoisobenzofuran-1(3H)-one, 3-heptylisobenzofuran-1(3H)-one, 3-butyl isobenzofuran-1(3H)-one, isobenzofuran-1,3-dione, 2-benzyl isoindoline-1,3-dione.

In the process for the synthesis of carboxylic acid derivatives stirring is carried out at temperature ranges from 100° C. to 120° C. for 10-12 hrs and dimethylformamide is used as polar solvent.

Dimethylformamide is used as polar solvent and quenching in step (b) is carried out using water. The reaction proceeds smoothly in presence of copper (I) salt in catalytic form. The halides according to the invention are selected from substituted or unsubstituted arylic, allylic, vinylic and alkylic halides and pseudohalides (like OMs, OTf) that have been found to support this transformation. The process of the instant invention as shown in scheme 1a and 1b will find tremendous application in carbonylative coupling processes acting as substitute for the hazardous Carbon monoxide.

The copper-catalyzed carbonylative coupling of halide derivatives in presence of CN source through intermolecular nucleophilic substitution is represented in general scheme 1a.

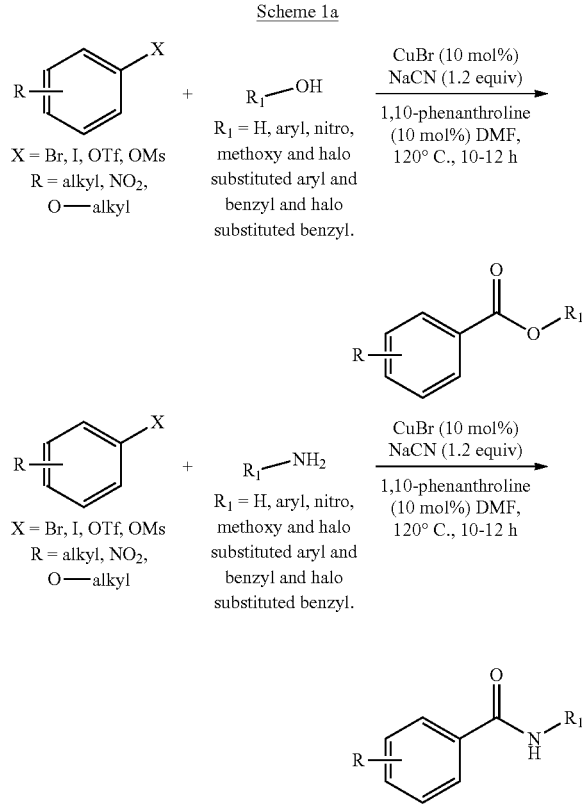

The copper catalyzed carbonylative coupling of halide derivatives in presence of CN source through intramolecular nucleophilic substitution is represented in general scheme 1b.

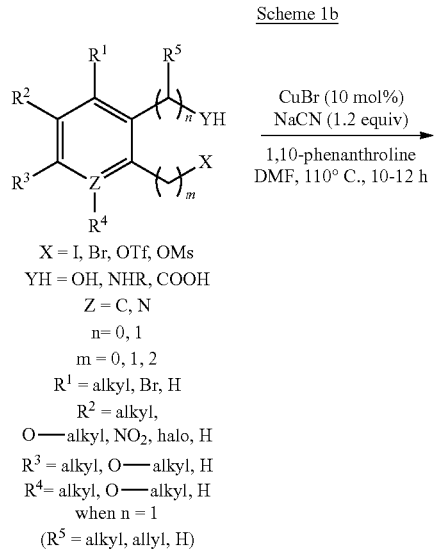

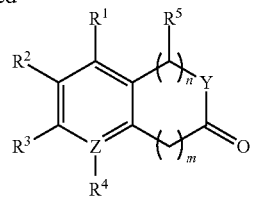

The tentative mechanism may be presumed that reaction sequence may involve a Cu insertion into the C—X bond followed by cyanation, then reductive elimination of Cu to give cyanated product which when attacked by O, N substituted nucleophile generates imine that undergoes hydrolysis on quenching the reaction mixture with water to give various carboxylic acid derivatives. The role of NaCN is crucial in the present application in order to obtain carbonylative coupling with a simultaneous C—C and C—O bond formation.

EXAMPLES

Following examples are given by way of illustration and therefore should not be construed to limit the scope of the invention.

Example 1: General Experimental Procedure for the Preparation of Carboxylic Acid Derivatives (3a-3k)

To a stirred solution of haloarenes 1a-1k (3 mmol) and nucleophiles 2a-2k (3 mmol) in dry DMF (15 mL) was added NaCN (3.3 mmol), CuBr (0.3 mmol, 10 mol %) and 1,10-phenanthroline (0.3 mmol, 10 mol %), the entire solution stirred at 120° C. under $N_2$ for 12 h (monitored by TLC). The reaction mixture was then cooled to room temperature (25° C.) and excess cyanide was quenched with aq. $NaClO_2$, diluted with water (10 mL) and EtOAc (15 mL). The organic layer was separated and the aqueous layer was extracted with EtOAc (3×20 mL). The combined organic extracts were washed with brine, dried over anhyd. $Na_2SO_4$ and concentrated under reduced pressure to give crude products which were purified by column chromatography [silica gel (230-400 mesh) and petroleum ether: EtOAc (7:3) as an eluent to afford corresponding esters and amides (3a-3k) in 63-76% yield.

TABLE 1

| No. | substrates (1a-1k) (ArX) (1 equiv) | nucleophiles (2a-2k) (RYH) (1 equiv) | Product (3a-3k) | yields (%) |
|---|---|---|---|---|
| a | bromobenzene | phenol | phenylbenzoate | 74 |
| b | bromobenzene | 4-$NO_2$-phenol | 4-$NO_2$-phenylbenzoate | 71 |
| c | bromobenzene | 4-OMe benzylalcohol | 4-OMe-benzylbenzoate | 76 |
| d | bromobenzene | aniline | benzanilide | 68 |
| e | bromobenzene | 2-Cl-aniline | 2-Cl-benzanilide | 70 |
| f | bromobenzene | 4-OMe-aniline | 4-OMe-benzanilide | 63 |
| g | bromobenzene | 2-Cl-benzylamine | 2-Cl-benzylbenzamide | 71 |
| h | bromobenzene | water | benzoic acid | 70 |
| i | 3-Br-toluene | phenol | 3-Me-phenylbenzoate | 68 |
| j | 4-MeO-bromobenzene | phenol | 4-MeO-phenylbenzoate | 71 |
| k | 4-$NO_2$-iodobenzene | phenol | 4-$NO_2$-phenylbenzoate | 71 |

Example 2: General Experimental Procedure for the Preparation of Carboxylic Acid Derivatives (3l-3z)

To a stirred solution of haloarenes 2l-2z (3 mmol) in dry DMF (15 mL) was added NaCN (3.3 mmol), CuBr (0.3 mmol) and 1,10-phenanthroline (0.3 mmol), the entire solution stirred at 120° C. under $N_2$ for 12 h (monitored by TLC). The reaction mixture was then cooled to room temperature (25° C.) and excess cyanide was quenched with aq. $NaClO_2$, diluted with water (10 mL) and EtOAc (15 mL). The organic layer was separated and the aqueous layer was extracted with EtOAc (3×20 mL). The combined organic extracts were washed with brine, dried over anhyd. $Na_2SO_4$ and concentrated under reduced pressure to give crude products which was purified by column chromatography [silica gel (230-400 mesh) and petroleum ether: EtOAc (7:3) as an eluent to afford corresponding esters and amides (3l-3z) in 73-96% yield.

TABLE 2

| No. | substrates (2l-2z) (1 equiv) | products (3l-3z) & Yields (%) |
|---|---|---|
| l-o | $R_1$ = H, $R_2$ = H; (2l)<br>$R_1$ = H, $R_2$ = Me; (2m)<br>$R_1$ = OMe, $R_2$ = H; (2n)<br>$R_1$ = F, $R_2$ = H; (2o) | $R_1$ = H, $R_2$ = H; (3l), 84%<br>$R_1$ = H, $R_2$ = Me; (3m), 86%<br>$R_1$ = OMe, $R_2$ = H; (3n), 87%<br>$R_1$ = F, $R_2$ = H; (3o), 88% |
| p | (2p) | (3p), 84% |
| q | (2q) | (3q), 84% |
| r | (2r) | (3r), 81% [c] |
| s-w | $R_1$ = F, $R_2$ = allyl; (2s)<br>$R_1$ = OMe, $R_2$ = allyl; (2t)<br>$R_1$ = Br, $R_2$ = allyl; (2u)<br>$R_1$ = H, $R_2$ = heptyl; (2v)<br>$R_1$ = H, $R_2$ = butyl; (2w) | $R_1$ = F, $R_2$ = allyl; (3s), 92%<br>$R_1$ = OMe, $R_2$ = allyl; (3t), 85%<br>$R_1$ = Br, $R_2$ = allyl; (3u), 78%<br>$R_1$ = H, $R_2$ = heptyl; (3v), 91%<br>$R_1$ = H, $R_2$ = butyl; (3w), 85% |
| x | (2x) | (3x), 96% |

TABLE 2-continued

| No. | substrates (2l-2z) (1 equiv) | products (3l-3z) & Yields (%) |
|---|---|---|
| y | 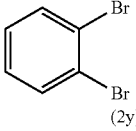 (2y) | 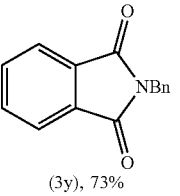 (3y), 73% |
| z | 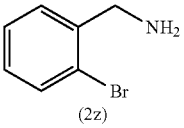 (2z) | 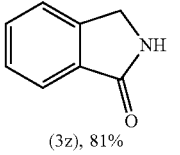 (3z), 81% |

[c] concomitant reduction of one of the Br to H takes place
[d] 2 equiv NaCN used, 1 equiv of benzylamine used as nucleophile.

Example 3: Phenyl Benzoate (3a)

Yield: 74% (0.440 g, 2.222 mmol); Colorless solid; mp. 70° C.; IR (CHCl$_3$, cm$^{-1}$): $\upsilon_{max}$ 690, 1080, 1260, 1500, 1718, 2980; $^1$H NMR (200 MHz, CHLOROFORM-d) δ 7.18-7.30 (m, 3H) 7.39-7.53 (m, 4H) 7.58-7.67 (m, 1H), 8.20 (td, J=1.7 and 6.9 Hz, 2H); $^{13}$C NMR (50 MHz, CHLOROFORM-d) δ 121.7, 125.8, 128.5, 129.4, 129.7, 130.2, 133.5, 151.0, 164.9; Analysis: C$_{13}$H$_{10}$O$_2$ requires C, 78.77; H, 5.09; O, 16.14; Found: C, 78.56; H, 5.34; O, 16.10%.

Example 4: 4-nitrophenyl benzoate (3b)

Yield: 71% (0.517 g, 2.127 mmol); Colorless solid; mp. 141° C.; IR (CHCl$_3$, cm$^{-1}$): $\upsilon_{max}$ 695, 1060, 1206, 1340, 1530, 1740, 3010; $^1$H NMR (200 MHz, CHLOROFORM-d) δ ppm 7.43 (td, J=3.2 and 8.9 Hz, 2H) 7.50-7.61 (m, 2H) 7.55 (dt, J=1.6 and 7.6 Hz, 1H) 7.70 (tt, J=1.6 and 7.6 Hz, 1H), 8.19-8.24 (m, 2H), 8.34 (td, J=3.2 and 8.9 Hz, 2H); $^{13}$C NMR (50 MHz, CHLOROFORM-d) δ 122.6, 125.2, 128.6, 128.8, 130.3, 134.2, 145.4, 155.7, 164.0; Analysis: C$_{13}$H$_9$NO$_4$ requires C, 64.20; H, 3.73; N, 5.76; O, 26.31; Found: C, 64.46; H, 3.54; N, 5.67; O, 26.33%.

Example 5: 4-methoxybenzyl benzoate (3c)

Yield: 76% (0.552 g, 2.280 mmol); Colorless solid; mp. 91° C.; IR (CHCl$_3$, cm$^{-1}$): $\upsilon_{max}$ 693, 1075, 1270, 1500, 1720, 2990; $^1$H NMR (200 MHz, CHLOROFORM-d) δ 3.80 (s, 3H), 5.28 (s, 2H), 6.89 (td, J=2.9 and 8.6 Hz, 2H), 7.35-7.45 (m, 4H), 7.53 (tt, J=1.7 and 7.1 Hz, 1H), 8.04 (td, J=1.7 and 7.1 Hz, 2H); $^{13}$C NMR (50 MHz, CHLOROFORM-d) δ 55.1, 66.4, 113.9, 128.2, 129.5, 129.6, 130.0, 130.3, 132.8, 159.6, 166.2; Analysis: C$_{15}$H$_{14}$O$_3$ requires C, 74.36; H, 5.82; O, 19.81; Found: C, 74.35; H, 5.78; O, 19.87%.

Example 6: N-phenylbenzamide (3d)

Yield: 68% (0.402, 2.040 mmol); Colorless solid; mp. 163° C.; IR(CHCl$_3$, cm$^{-1}$): $\upsilon_{max}$ 690, 780, 1305, 1430, 1530, 1600, 1670, 3330; $^1$H NMR (200 MHz, CHLOROFORM-d) δ ppm 6.63-6.77 (m, 2H), 7.13 (tt, J=1.6 and 8.4 Hz, 2H), 7.32-7.65 (m, 5H), 7.86 (td, J=1.6 and 6.4 Hz, 2H); $^{13}$C NMR (100 MHz, CHLOROFORM-d) δ 115.1, 118.6, 120.2, 124.6, 127.1, 128.8, 129.1, 129.3, 131.8, 135.1, 138.0, 146.3, 165.5; Analysis: C$_{13}$H$_{11}$NO requires C, 79.17; H, 5.62; N, 7.10; O, 8.11; Found: C, 79.95; H, 5.54; N, 7.13; O, 7.38%.

Example 7: N-(2-chlorophenyl)benzamide (3e)

Yield: 70% (0.486 g, 2.099 mmol); Colorless solid; mp. 101° C.; IR (CHCl$_3$, cm$^{-1}$): $\upsilon_{max}$ 690, 788, 1310, 1415, 1510, 1600, 1680, 3310; $^1$H NMR (200 MHz, CHLOROFORM-d) δ 7.07 (dt, J=1.3 and 7.4 Hz, 1H), 7.29-7.59 (m, 5H), 7.93 (td, J=1.3 and 6.1 Hz, 2H), 8.45 (br. s., 1H), 8.58 (dd, J=1.6 and 8.3 Hz, 1H); $^{13}$C NMR (100 MHz, CHLOROFORM-d) δ 121.5, 122.9, 124.6, 127.1, 127.9, 128.9, 128.9, 132.1, 134.6, 134.8, 165.0; Analysis: C$_{13}$H$_{10}$ClNO requires C, 67.40; H, 4.35; Cl, 15.30; N, 6.05; O, 6.91 Found: C, 67.87; H, 4.23; Cl, 15.18; N, 6.20; O, 6.52%.

Example 8: N-(4-methoxyphenyl)benzamide (3f)

Yield: 63% Colorless solid; IR (CHCl$_3$, cm$^{-1}$): $\upsilon_{max}$ 690, 708, 1320, 1411, 1530, 1610, 1670, 3210; $^1$H NMR (200 MHz, CHLOROFORM-d) 9.8 (s, 1H), 6.8-8.0 (m, 9H), 3.8 (s, 3H).

Example 9: N-(2-chlorobenzyl)benzamide (3g)

Yield: 71% (0.523 g, 2.130 mmol); Colorless solid; mp. 99° C.; IR (CHCl$_3$, cm$^{-1}$): $\upsilon_{max}$ 688, 785, 1316, 1400, 1520, 1678, 3320; $^1$H NMR (200 MHz, CHLOROFORM-d) δ 4.70 (d, J=5.4 Hz, 2H), 6.73 (br. s., 1H) 7.20-7.26 (m, 2H) 7.35-7.52 (m, 5H) 7.77 (dd, J=1.6 and 8.2 Hz, 2H); $^{13}$C NMR (100 MHz, CHLOROFORM-d) δ 42.0, 127.0, 127.1, 128.6, 128.9, 129.6, 130.4, 131.5, 133.7, 134.3, 135.7, 167.2; Analysis: C$_{14}$H$_{12}$ClNO requires C, 68.44; H, 4.92; Cl, 14.43; N, 5.70; O, 6.51 Found: C, 68.87; H, 4.23; Cl, 14.78; N, 5.20; O, 6.92%.

Example 10: Benzoic Acid (3h)

Yield: 70% (0.256 g, 2.098 mmol); Colorless solid; mp. 123° C.; IR (CHCl$_3$, cm$^{-1}$): $\upsilon_{max}$ 700, 1280, 1320, 1410, 1690, 3200; $^1$H NMR (400 MHz, ACETONE-d$_6$) δ ppm 7.43-7.48 (m, 2H), 7.50-7.55 (m, 1H), 7.93-7.96 (m, 2H); $^{13}$C NMR (50 MHz, Acetone) δ 30.2, 128.3, 129.1, 132.1, 135.3, 169.1; Analysis: $C_7H_6O_2$ requires C, 68.85; H, 4.95; O, 26.20 Found: C, 68.82; H, 4.97; O, 26.21%.

Example 11: phenyl 3-methylbenzoate (3i)

Yield: 68% (0.433 g, 2.041 mmol); Colorless oil; $^1$H NMR (200 MHz, CHLOROFORM-d) δ ppm 2.45 (s, 3H), 7.16-7.30 (m, 3H), 7.34-7.46 (m, 4H), 7.98-8.01 (m, 2H); $^{13}$C NMR (50 MHz, CHLOROFORM-d) δ 21.0, 121.5, 125.5, 127.0, 128.2, 129.1, 129.2, 130.4, 134.0, 137.9, 150.8, 164.7; Analysis: $C_{14}H_{12}O_2$ requires C, 79.23; H, 5.70; O, 15.08 Found: C, 79.12; H, 5.97; O, 14.91%.

Example 12: phenyl 4-methoxybenzoate (3j)

Yield: 71% (0.485 g, 2.130 mmol); Colorless solid; mp. 70° C.; $^1$H NMR (200 MHz, CHLOROFORM-d) δ ppm 3.89 (s, 3H), 6.97 (td, J=3.5 Hz and 9.1 Hz, 2H), 7.15-7.29 (m, 3H), 7.35-7.46 (m, 2H); $^{13}$C NMR (125 MHz, CHLOROFORM-d) δ 55.4, 113.8, 121.8, 123.2, 125.7, 129.4, 132.3, 151.1, 163.9, 164.7; Analysis: $C_{14}H_{12}O_3$ requires C, 73.67; H, 5.30; O, 21.03 Found: C, 73.75; H, 5.13; O, 21.12%.

Example 13: phenyl 4-nitrobenzoate (3k)

Yield: 71% (0.518 g, 2.130 mmol); Colorless solid; mp. 128° C.; $^1$H NMR (200 MHz, CHLOROFORM-d) δ ppm 7.16-7.50 (m, 5H), 8.36 (s, 4H); $^{13}$C NMR (125 MHz, CHLOROFORM-d) δ122.8, 123.8, 129.8, 131.3, 131.9, 134.6, 148.9, 151.0, 162.9; Analysis: $C_{13}H_9NO_4$ requires C, 64.20; H, 3.73; N, 5.76; O, 26.31 Found: C, 64.38; H, 3.52; N, 5.81; O, 26.29%.

Example 14: 3-allylisochroman-1-one (3l)

Yield: 86% (0.474 g, 2.521 mmol); Colorless oil; IR (CHCl$_3$, cm$^{-1}$): $\upsilon_{max}$ 745, 1118, 1281, 1723, 2918, 3077; $^1$H NMR (200 MHz, CHLOROFORM-d) δ 2.45-2.72 (m, 2H) 2.87-3.07 (m, 2H) 4.51-4.62 (m, 1H), 5.13-5.24 (m, 2H), 5.79-5.97 (m, 1H) 7.21-7.56 (m, 3H), 8.07 (dd, J=0.8 and 7.7 Hz, 1H); $^{13}$C NMR (125 MHz, CHLOROFORM-d): δ 32.5, 39.2, 77.6, 118.8, 125.2, 127.3, 127.6, 130.3, 132.3, 133.6, 138.9, 164.9; HRMS (ESI+, m/z): calcd for $(C_{12}H_{12}O_2)^+$ [(M+Na)$^+$] 211.0727; found: 211.0730; Analysis: $C_{12}H_{12}O_2$ requires C, 76.57; H, 6.43; O, 17.00 Found: C, 76.58; H, 6.33; O, 17.09%.

Example 15: 3-allyl-7-methylisochroman-1-one (3m)

Yield: 86% (0.521 g, 2.579 mmol); Colorless oil; IR (CHCl$_3$, cm$^{-1}$): $\upsilon_{max}$ 774, 921, 1082, 1194, 1723, 2923, 3078; $^1$H NMR (200 MHz, CHLOROFORM-d) δ 2.39 (s, 3H), 2.51-2.68 (m, 2H), 2.82-2.94 (m, 2H), 4.48-4.61 (m, 1H), 5.12-5.23 (m, 2H), 5.77-6.00 (m, 1H) 7.10 (d, J=7.7 Hz, 1H) 7.32 (d, J=7.7 Hz, 1H), 7.90 (s, 1H); $^{13}$C NMR (50 MHz, CHLOROFORM-d) δ 20.9, 32.1, 39.2, 77.7, 118.7, 124.8, 127.2, 130.4, 132.4, 134.4, 135.9, 137.3, 165.2; HRMS (ESI+, m/z): calcd for $(C_{13}H_{14}O_2)^+$ [(M+Na)$^+$] 225.0884; found: 225.0886; Analysis: $C_{13}H_{14}O_2$ requires C, 77.20; H, 6.98; O, 15.82 Found: C, 77.38; H, 6.83; O, 15.79%.

Example 16: 3-allyl-6-methoxyisochroman-1-one (3n)

Yield: 87% (0.569 g, 2.610 mmol); Colorless oil; IR (CHCl$_3$, cm$^{-1}$): $\upsilon_{max}$ 778, 917, 1027, 1260, 1606, 1716, 2920, 3076; $^1$H NMR (200 MHz, CHLOROFORM-d) δ 2.48-3.04 (m, 4H), 3.86 (s, 3H), 4.49-4.60 (m, 1H), 5.16-5.24 (m, 2H), 5.83-6.00 (m, 1H), 6.70 (d, J=2.4 Hz, 1H), 6.87 (dd, J=2.4 and 8.3 Hz, 1H), 8.02 (d, J=8.3 Hz, 1H); $^{13}$C NMR (50 MHz, CHLOROFORM-d) δ 32.7, 39.1, 55.4, 77.4, 112.0 113.4, 117.5, 118.7, 132.3, 132.4, 141.2, 163.7, 165.3; HRMS (ESI+, m/z): calcd for $(C_{13}H_{14}O_3)^+$ [(M+Na)$^+$] 241.0831; found: 241.0835; Analysis: $C_{13}H_{14}O_3$ requires C, 71.54; H, 6.47; O, 21.99 Found: C, 71.58; H, 6.53; O, 21.89%.

Example 17: 3-allyl-6-fluoroisochroman-1-one (3o)

Yield: 88% (0.536 g, 2.640 mmol); Colorless oil; IR (CHCl$_3$, cm$^{-1}$): $\upsilon_{max}$ 667, 755, 1107, 1267, 1615, 1725, 2919, 3079; $^1$H NMR (200 MHz, CHLOROFORM-d) δ 2.45-2.72 (m, 2H) 2.84-3.08 (m, 2H), 4.51-4.65 (m, 1H), 5.16-5.25 (m, 2H), 5.78-5.99 (m, 1H), 6.93 (dd, J=2.3 and 8.1 Hz, 1H), 7.06 (dt, J=2.3 and 8.1 Hz, 1H), 8.10 (dd, J=5.6 and 8.6 Hz, 1H); $^{13}$C NMR (125 MHz, CHLOROFORM-d) δ 32.6, 39.1, 77.5, 114.3, 115.3, 119.1, 121.5, 132.1, 133.3, 141.9, 164.0, 166.8; HRMS (ESI+, m/z): calcd for $(C_{12}H_{11}O_2F)^+$ [(M+Na)$^+$] 229.0632; found: 229.0635; Analysis: $C_{12}H_{11}O_2F$ requires C, 69.89; H, 5.38; F, 9.21; O, 15.52 Found: C, 69.95; H, 5.54; F, 9.13; O, 15.38%.

Example 18: 6,7,8-trimethoxy-1-oxoisochromane-5-carbonitrile (3p)

Yield: 84% (0.663 g, 2.520 mmol); yellowish solid; mp. 107° C.; IR (CHCl$_3$, cm$^{-1}$): $\upsilon_{max}$ 802, 1036, 1130, 1579, 1677, 1713, 2922, 2949; $^1$H NMR (200 MHz, CHLOROFORM-d) δ 3.31 (t, J=8.5 Hz, 2H), 3.85 (s, 3H), 3.95 (s, 3H), 4.04 (s, 3H), 4.65 (t, J=8.5 Hz, 2H); $^{13}$C NMR (125 MHz, CHLOROFORM-d) δ 27.4, 61.4, 61.8, 62.2, 65.7, 100.3, 113.8, 115.2, 141.2, 145.1, 159.6, 159.7, 161.2; HRMS (ESI+, m/z): calcd for $(C_{13}H_{13}NO_5)^+$ [(M+Na)$^+$] 286.0691; found: 286.0693; Analysis: $C_{13}H_{13}NO_5$ requires C, 59.31; H, 4.98; N, 5.32; O, 30.39 Found: C, 58.95; H, 4.57; N, 5.27; O, 31.21%.

Example 19: 6-allyl-5,6-dihydro-8H-pyrano[3,4-b]pyridin-8-one (3q)

Yield: 84% (0.476 g, 2.518 mmol); yellow oil; $^1$H NMR (200 MHz, CHLOROFORM-d) □ 2.29-2.73 (m, 4H), 5.05-5.19 (m, 2H), 5.23 (s, 1H), 5.79-5.96 (m, 1H), 7.27 (dd, J=4.9 and 7.6 Hz, 1H), 7.92 (dd, J=1.5 Hz and 7.6 Hz, 1H), 8.28 (dd, J=1.5 and 4.9 Hz, 1H); $^{13}$C NMR (125 MHz, CHLOROFORM-d) δ 40.4, 42.0, 69.3, 118.9, 122.4, 133.3, 134.0, 140.4, 147.7, 151.5; Analysis: $C_9H_6O_2$ requires C, 73.97; H, 4.14; O, 21.89; Found: C, 73.94; H, 4.17; O, 21.89%.

Example 20: 2H-chromen-2-one (3r)

Yield: 81% (0.355 g, 2.430 mmol); Colorless liquid; IR (CHCl$_3$, cm$^{-1}$): $\upsilon_{max}$ 820, 1104, 1180, 1610, 1710, 3030; $^1$H NMR (200 MHz, CHLOROFORM-d) δ 6.43 (d, J=9.4 Hz, 1H), 7.28-7.57 (m, 4H), 7.77 (d, J=9.4 Hz, 1H); $^{13}$C NMR (50 MHz, CHLOROFORM-d) δ 116.7, 116.9, 118.8, 124.4, 127.8, 131.8, 143.5, 154.0, 160.8; Analysis: $C_9H_6O_2$ requires C, 73.97; H, 4.14; O, 21.89; Found: C, 73.94; H, 4.17; O, 21.89%.

Example 21:
3-allyl-5-fluoroisobenzofuran-1(3H)-one (3s)

Yield: 92% (0.530 g, 2.760 mmol); Colorless oil; IR (CHCl$_3$, cm$^{-1}$): $υ_{max}$ 988, 1100, 1247, 1483, 1604, 1624, 1766, 3100; $^1$H NMR (200 MHz, CHLOROFORM-d) δ 2.62-2.78 (m, 2H), 5.12-5.25 (m, 2H), 5.48 (t, J=6.1 Hz, 1H), 5.65-5.86 (m, 1H), 7.12-7.28 (m, 2H), 7.89 (dd, J=4.8 and 8.1 Hz, 1H); $^{13}$C NMR (50 MHz, CHLOROFORM-d) δ 38.2, 79.2, 109.3, 117.2, 119.8, 122.2, 127.8, 130.6, 151.9, 163.6, 168.7; Analysis: $C_{11}H_9FO_2$ requires C, 68.75; H, 4.72; F, 9.89; O, 16.65; Found: C, 68.82; H, 4.97; O, 26.21%.

Example 22:
3-allyl-5-methoxyisobenzofuran-1(3H)-one (3t)

Yield: 85% (0.518 g, 2.551 mmol); Colorless oil; IR (CHCl$_3$, cm$^{-1}$): $υ_{max}$ 692, 1073, 1103, 1259, 1605, 1744, 2997; $^1$H NMR (200 MHz, CHLOROFORM-d) δ ppm 2.56-2.81 (m, 2H), 3.91 (s, 3H), 5.15-5.25 (m, 2H), 5.42 (t, J=6.1 Hz, 1H), 5.68-5.89 (m, 1H), 6.87 (d, J=1.6 Hz, 1H), 7.02 (dd, J=1.6 and 8.5 Hz, 1H), 7.80 (d, J=8.5 Hz, 1H); $^{13}$C NMR (50 MHz, CHLOROFORM-d) δ 38.8, 55.7, 79.3, 106.1, 116.2, 118.7, 119.6, 127.2, 131.3, 152.0, 164.5, 169.8; Analysis: $C_{12}H_{12}O_3$ requires C, 70.58; H, 5.92; O, 23.50; Found: C, 70.61; H, 5.67; O, 23.72%.

Example 23: 5-bromoisobenzofuran-1(3H)-one (3u)

Yield: 78% (0.498 g, 2.338 mmol); Colorless solid; mp. 162° C.; $^1$H NMR (200 MHz, CHLOROFORM-d) δ ppm 5.30 (s, 2H), 7.68 (t, J=3.7 Hz, 2H), 7.77-7.81 (m, 1H); $^{13}$C NMR (50 MHz, CHLOROFORM-d) δ 68.8, 124.9, 125.6, 127.1, 129.2, 132.7, 148.2, 169.7; Analysis: $C_8H_5BrO_2$ requires C, 45.11; H, 2.37; Br, 37.51; O, 15.02 Found: C, 45.65; H, 2.24; Br, 38.13; O, 13.98%.

Example 24: 3-heptylisobenzofuran-1(3H)-one (3v)

Yield: 91% (0.633 g, 2.728 mmol); Colorless oil; $^1$H NMR (200 MHz, CHLOROFORM-d) δ ppm 0.88 (t, J=3.5 Hz, 3H), 1.27-1.47 (m, 10H), 1.66-1.82 (m, 1H), 1.96-2.12 (m, 1H), 5.46 (dd, J=4.0 and 7.4 Hz, 1H), 7.41-7.55 (m, 2H), 7.66 (dt, J=1.6 and 7.6 Hz, 1H). 7.88 (d, J=7.6 Hz, 1H); $^{13}$C NMR (50 MHz, CHLOROFORM-d) δ 14.0, 22.5, 24.8, 29.0, 29.3, 31.7, 34.7, 81.2, 121.6, 125.6, 126.2 128.9, 133.8, 150.0, 170.3; Analysis: $C_{15}H_{20}O_2$ requires C, 77.55; H, 8.68; O, 13.77 Found: C, 77.58; H, 8.71; O, 13.71%.

Example 25: 3-butylisobenzofuran-1(3H)-one (3w)

Yield: 87% (0.496 g, 2.610 mmol); Colorless oil; $^1$H NMR (200 MHz, CHLOROFORM-d) δ 0.91 (t, J=6.3 Hz, 3H), 1.26-1.52 (m, 4H), 1.71-1.82 (m, 1H), 1.98-2.12 (m, 1H), 5.46 (dd, J=4.1 and 7.2 Hz, 1H), 7.50 (dd, J=7.2 and 9.8 Hz, 2H), 7.67 (t, J=7.2 Hz, 1H), 7.88 (d, J=7.8 Hz, 1H); $^{13}$C NMR (50 MHz, CHLOROFORM-d) δ 13.8, 22.4, 26.8, 34.4, 81.2, 121.6, 125.6, 126.2, 128.9, 133.8, 150.0, 170.2; Analysis: $C_{12}H_{14}O_2$ requires C, 75.76; H, 7.42; O, 16.82; Found: C, 75.54; H, 7.57; O, 16.89%.

Example 26: isobenzofuran-1,3-dione (3x)

Yield: 96% (0.426 g, 2.878 mmol); Colorless solid; mp. 131° C.; IR (CHCl$_3$, cm$^{-1}$): $υ_{max}$ 667, 758, 1052, 1307, 1604, 1748, 1772, 2924; $^1$H NMR (200 MHz, CHLOROFORM-d) δ 7.77 (dd, J=2.0 and 6.0 Hz, 2H), 7.89 (dd, J=2.0 and 6.0 Hz, 2H); $^{13}$C NMR (100 MHz, CHLOROFORM-d) δ 123.6, 132.7, 134.28, 167.7; HRMS (ESI+, m/z): calcd for $(C_8H_5O_3)^+$ 149.0232; found: 149.0233; Analysis: $C_8H_4O_3$ requires C, 64.87; H, 2.72; O, 32.40; Found: C, 64.82; H, 2.77; O, 32.41%.

Example 27: 2-benzylisoindoline-1,3-dione (3y)

Yield: 73% (0.396 g, 2.187 mmol); Colorless solid; mp. 115° C.; IR(CHCl$_3$, cm$^{-1}$): 717, 1062, 1331, 1391, 1453, 1715, 1764, 2853, 2924; $^1$H NMR (200 MHz, CHLOROFORM-d) δ 4.84 (s, 2H), 7.24-7.45 (m, 5H), 7.69 (dd, J=2.9 and 5.6 Hz, 2H), 7.84 (dd, J=2.9 and 5.6 Hz, 2H); $^{13}$C NMR (50 MHz, CHLOROFORM-d) δ 41.6, 123.3, 127.8, 128.7, 132.2, 133.9, 136.4, 167.9; HRMS (ESI+, m/z): calcd for $(C_{15}H_{11}O_2NNa)^+$ $[(M+Na)^+]$ 260.0678; found: 260.0682; Analysis: $C_{15}H_{11}NO_2$ requires C, 75.94; H, 4.67; N, 5.90; O, 13.49; Found: C, 75.87; H, 4.33; N, 5.98; O, 13.82%.

Example 28: isoindolin-1-one (3z)

1H NMR (CDCl3, 400 MHz) δ 4.41 (s, 2H), 7.41-7.53 (m, 4H), 7.81 (d, J=7.6 Hz, 1H); $^{13}$C NMR (CDCl3, 100 MHz) δ (ppm) 45.7, 123.2, 123.7, 128.0, 131.7, 132.1, 143.6, 172.0.

Example 29: Intramolecular Carbonylative Coupling of 1-(2-bromophenyl)pent-4-en-2-ol Optimization Studies[a]

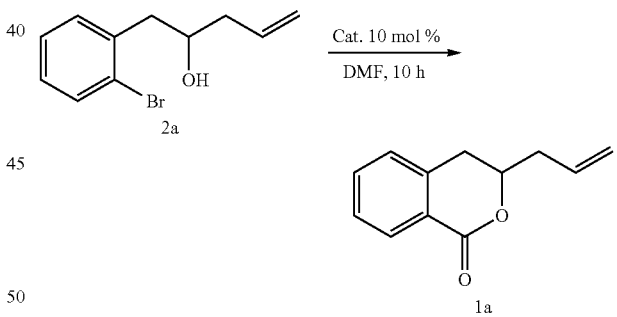

TABLE 3

CuBr-catalyzed carbonylative coupling of bromobenzene with phenol using NaCN as $C_1$ source: optimization studies

| Entry | Catalyst | CN source (equiv.) | Temp. (° C.) | Yield (%)[b] |
|---|---|---|---|---|
| 1. | — | CuCN (1.0) | 150 | 28 |
| 2. | — | CuCN (2.0) | 150 | 53 |
| 3. | — | CuCN (3.0) | 150 | 85 (trace)[c] |
| 4. | — | CuCN (3.5) | 150 | 85 |
| 5. | — | CuCN (3.0) | 120 | 48 |
| 6. | Cu(OAc)$_2$ | K$_4$[Fe(CN)$_6$] (0.5) | 110 | trace |
| 7. | CuBr | NaCN (1.1) | 150 | 70 |

TABLE 3-continued

CuBr-catalyzed carbonylative coupling of bromobenzene with phenol using NaCN as $C_1$ source: optimization studies

| Entry | Catalyst | CN source (equiv.) | Temp. (° C.) | Yield (%)[b] |
|---|---|---|---|---|
| 8. | CuBr + 1,10-phenanthroline (0.1) | NaCN (1.1) | 110 | 84 |
| 9. | CuBr + L-proline (0.1) | NaCN (1.1) | 110 | 70 |

[a]Alcohol1a (1 equiv), Catalyst (10 mol %), CN source, 12 h.
[b]Isolated yield after column chromatography purification.
[c]DMSO used as solvent.

It is worth mentioning that intramolecular reactions afforded products in better yields than intermolecular reactions.

ADVANTAGES OF THE INVENTION

A facile process for carbonylative coupling.
Hazardous Carbon monoxide free carbonylation reaction.
One-step, one-pot and simple process for carbonylative coupling.
The present invention reports Cu catalyzed preparation of various carboxylic acid derivatives from arylic, vinylic and alkylic halide using NaCN as the cyanide source for bringing in carbonylative coupling in a single step.
This process will find tremendous application in carbonylative coupling processes acting as substitute for the hazardous Carbon monoxide.

We claim:

1. A one-step, one-pot process for the synthesis of carboxylic acid or carboxylic acid derivatives comprising the steps of:
    a. stirring the solution of 0.9-1.1 equivalent aryl halides in dimethylformamide (DMF) optionally in the presence of 0.9-1.3 equivalent nucleophile followed by addition of 1.0-1.2 equivalent sodium cyanide and 10-20 mol % of 1, 10-phenanthroline and 5-25 mol % of copper bromide; and
    b. quenching the reaction mixture of step (a) to obtain carboxylic acid or carboxylic acid derivatives, wherein the nucleophile is selected from the group consisting of water, phenol, 4-nitro-phenol, 4-methoxybenzyl alcohol, aniline, 2-chloro-aniline, 4-methoxy-aniline, and 2-chloro-benzylamine.

2. The process according to claim 1, wherein the halides are selected from the group consisting of bromobenzene, 3-bromo-toluene, 4-methoxy-bromobenzene, 4-nitro-iodobenzene, 1-(2-bromophenyl)pent-4-en-2-ol, 1-(2-bromo-5-methylphenyl)pent-4-en-2-ol, 1-(2-bromo-5-methoxyphenyl)pent-4-en-2-ol, 1-(2-bromo-5-fluorophenyl)pent-4-en-2-ol, 1-(2,6-dibromo-3,4,5-trimethoxyphenyl)pent-4-en-2-ol, 1-(2-bromopyridin-3-yl)pent-4-en-2-ol, 2-(2,2-dibromovinyl)phenol, 1-(2-bromo-5-fluorophenyl)but-3-en-1-ol, 1-(2-bromo-5-methoxyphenyl)but-3-en-1-ol, 1-(2,5-dibromophenyl)but-3-en-1-ol, 1-(2-bromophenyl)octan-1-ol, 1-(2-bromophenyl)pentan-1-ol, 2-iodobenzoic acid, 1,2-dibromobenzene, and (2-bromophenyl)methanamine.

3. The process according to claim 1, wherein the carboxylic acid or carboxylic acid derivatives are selected from the group consisting of phenyl benzoate, 4-nitrophenyl benzoate, 4-methoxybenzyl benzoate, N-phenylbenzamide, N-(2-chlorophenyl)benzamide, N-(2-chlorobenzyl)benzamide, benzoic acid, phenyl 3-methylbenzoate, phenyl 4-methoxybenzoate, phenyl 4-nitrobenzoate, 3-allylisochroman-1-one, 3-allyl-7-methylisochroman-1-one, 3-allyl-6-methoxyisochroman-1-one, 3-allyl-6-fluoroisochroman-1-one, 6,7,8-trimethoxy-1-oxoisochromane-5-carbonitrile, 6-allyl-5,6-dihydro-8H-pyrano[3,4-b]pyridin-8-one, 2H-chromen-2-one, 3-allyl-5-fluoroisobenzofuran-1(3H)-one, 3-allyl-5-methoxyisobenzofuran-1(3H)-one, 5-bromoisobenzofuran-1(3H)-one, 3-heptylisobenzofuran-1(3H)-one, 3-butylisobenzofuran-1(3H)-one, isobenzofuran-1,3-dione, and 2-benzylisoindoline-1,3-dione.

4. The process according to claim 1, wherein the stirring in step (a) is carried out at temperature ranging from 100° C. to 120° C.

5. The process according to claim 1, wherein the stirring in step (a) is carried out for the period ranging from 10-12 hrs.

6. The process according to claim 1, wherein the quenching in step (b) is carried out using water.

7. The process according to claim 1, wherein yield is in the range of 63 to 96%.

* * * * *